US011210865B2

(12) United States Patent
Cavallo et al.

(10) Patent No.: US 11,210,865 B2
(45) Date of Patent: Dec. 28, 2021

(54) VISUALLY INTERACTING WITH THREE DIMENSIONAL DATA IN AUGMENTED OR VIRTUAL REALITY

(71) Applicant: International Business Machines Corporation, Armonk, NY (US)

(72) Inventors: Marco Cavallo, Santa Clara, CA (US); James R. Kozloski, New Fairfield, CT (US); Stephen J. Heisig, Tarrytown, NY (US)

(73) Assignee: International Business Machines Corporation, Armonk, NY (US)

(*) Notice: Subject to any disclaimer, the term of this patent is extended or adjusted under 35 U.S.C. 154(b) by 140 days.

(21) Appl. No.: 16/592,758

(22) Filed: Oct. 3, 2019

(65) Prior Publication Data
US 2021/0104102 A1 Apr. 8, 2021

(51) Int. Cl.
G06T 19/00 (2011.01)
G06T 19/20 (2011.01)
G06T 15/40 (2011.01)
G06T 15/00 (2011.01)
G06F 3/038 (2013.01)

(52) U.S. Cl.
CPC .............. *G06T 19/20* (2013.01); *G06F 3/038* (2013.01); *G06T 15/005* (2013.01); *G06T 15/40* (2013.01); *G06T 19/006* (2013.01); *G06F 2203/0384* (2013.01); *G06T 2219/2021* (2013.01)

(58) Field of Classification Search
None
See application file for complete search history.

(56) References Cited

U.S. PATENT DOCUMENTS

| 6,154,723 A | 11/2000 | Cox et al. |
| 6,798,412 B2 | 9/2004 | Cowperthwaite |
| 8,819,591 B2 | 8/2014 | Wang et al. |

(Continued)

OTHER PUBLICATIONS

M. Cavallo, HoloBrain: A 3D System for Brain Image Analysis, Accessed Jan. 28, 2019, 1 page http://www.mastercava.it/projects#augmentedreality.

(Continued)

*Primary Examiner* — Sarah Le
(74) *Attorney, Agent, or Firm* — Kristofer Haggerty; Otterstedt, Wallace & Kammer, LLP (57) ABSTRACT

An apparatus includes: a memory embodying three-dimensional data and computer executable instructions; sensors detecting a movable controller in a real space; at least one processor, operative by the computer executable instructions to facilitate: mapping the three dimensional data to a virtual space; tracking a real position and orientation of the movable controller using data from the sensors; converting the real position and orientation into a virtual position and orientation relative to the three dimensional data; identifying a selected region of the three dimensional data, which is tethered to the virtual position and orientation; and rendering the three dimensional data in the virtual space, with the selected region being rendered differently from the remainder of the three dimensional data; and showing a user the rendering of the three dimensional data in the virtual space by activating a virtual or augmented reality display that is activated by the at least one processor.

17 Claims, 6 Drawing Sheets

(56) References Cited

U.S. PATENT DOCUMENTS

| | | | |
|---|---|---|---|
| 2002/0082498 | A1 | 6/2002 | Wendt et al. |
| 2011/0107270 | A1* | 5/2011 | Wang ............... G16H 20/40 715/850 |
| 2018/0053343 | A1* | 2/2018 | Ren .................. G06T 11/001 |
| 2018/0140362 | A1 | 5/2018 | Cali et al. |
| 2019/0251755 | A1* | 8/2019 | Douglas ............ G06F 30/00 |
| 2020/0051337 | A1* | 2/2020 | Reynolds .......... G06F 3/011 |
| 2020/0174583 | A1* | 6/2020 | Wang ................ G06F 3/011 |

OTHER PUBLICATIONS

M. Sousa et al., "VRRRRoom: Virtual Reality for Radiologists in the Reading Room." In Proceedings of the 2017 CHI Conference on Human Factors in Computing Systems (CHI '17). ACM, NY, pp. 4057-4062, May 2017. DOI: https://doi.org/101145/3025453.3025566.

C. Ong et al., "Virtual Reality in Neurointervention," Journal of vascular and interventional neurology vol. 10,Jun. 1, 2018, pp. 17-22.

T. Tawara et al. "A framework for volume segmentation and visualization using Augmented Reality," 2010 IEEE Symposium on 3D User Interfaces (3DUI), Waltham, MA, Mar. 2010, pp. 121-122. doi: 10.1109/3DUI.2010.5444707.

S. Pidhorsky et al., "syGlass: Interactive Exploration of Multidimensional Images Using Virtual Reality Head-mounted Displays." (Submitted on Apr. 23, 2018 (v1), last revised Aug. 22, 2018 (this version, v4)), 9 pages https://arxiv.org/abs/1804.08197.

D. Duncan et al., "VRAIN: Virtual reality assisted intervention for neuroimaging," 2017 IEEE Virtual Reality (VR), Los Angeles, CA, Mar. 2017, pp. 467-468. doi: 10.1109/VR.2017.7892382.

Wikipedia—Hidden-surface determination specifically Occlusion culling, downloaded Apr. 30, 2019, 4 pages https://en.wikipedia.org/wiki/Hidden_surface_determination#Occlusion_culling.

S. Zhang et al., "An immersive virtual environment for DT-MRI volume visualization applications: a case study." In Proceedings Visualization, 2001. VIS'01. Oct. 21, 2001 (pp. 437-584). Ieee.

E. Olshannikova, et al., "Visualizing Big Data with augmented and virtual reality: challenges and research agenda." Journal of Big Data. Dec. 2015;2(1):22-48.

G. Conte, et al. "BRAINtrinsic: A virtual reality-compatible tool for exploring intrinsic topologies of the human brain connectome." In International Conference on Brain Informatics and Health Aug. 30, 2015 (pp. 67-76). Springer, Cham.

W. Usher, et al., "A virtual reality visualization tool for neuron tracing." IEEE transactions on visualization and computer graphics Aug. 29, 2017;24(1):994-1003.

M. Cavallo, et al. "Dataspace: A Reconfigurable Hybrid Reality Environment for Collaborative Information Analysis," arXiv:1903.03700v1 Mar. 2019, p. 1-10.

Google, "Search Results," https://www.google.com/search?q=holobrain+ibm, Oct. 2019, 1 page.

P. Mell, et al., "The NIST Definition of Cloud Computing," National Institute of Standards and Technology, U.S. Dept. of Commerce, Special Publication 800-145, Sep. 2011, p. 1-7.

* cited by examiner

VISUALLY INTERACTING WITH THREE DIMENSIONAL DATA IN AUGMENTED OR VIRTUAL REALITY

BACKGROUND

The present invention relates to the electrical, electronic, and computer arts, and more specifically, to presentation and analysis of three dimensional data.

Three dimensional data, such as mechanical stress/strain simulation data, ultrasound image data, magnetic resonance imaging (MRI) scan data, or thermal simulation data, is frequently used in science and industry to enhance workers' understanding of subject matter (such as, e.g., likelihood of system failure or patient health conditions). For example, in the medical arts, brain MRI data is used for patient health assessments, surgery planning, and education; obstetric ultrasound data is used for assessing fetal health and scheduling a delivery date. In the mechanical arts, ultrasound inspection data for an aircraft fuselage may be used to detect potential points of airframe failure.

Three dimensional data is composed of dense point clouds that are cumbersome to explore and analyze through existing bi-dimensional projection methods. A traditional method for rendering three dimensional data is ray tracing, which discloses the "visible" surface of a three dimensional data set for a given vantage point.

In order to visualize internal structures of three dimensional data according to certain known methods, the data can be "sliced" and rendered in two dimensional planes orthogonal to x-y-z axes. In medical imaging (e.g., brain data), this slicing approach arises from traditional preparation of brain specimens as slices in coronal, horizontal, or sagittal planes. Such slices are familiar and useful to students of medicine and neuroanatomy from standard atlases for learning gross anatomy of the brain. Such atlases often also are used for planning neurosurgical interventions. Occasionally, brain specimens have been sliced at intermediate angles in order to better show connectivity between brain areas that do not lie on the same standard slicing plane.

Some recent visualization tools improve on the traditional brain atlases by presenting a three dimensional rendering of a brain in combination with two dimensional slicing of the rendering. In this case, a user can rotate the brain and observe planar slices from various angles.

SUMMARY

Principles of the invention provide techniques for visually interacting with three dimensional data in augmented or virtual reality. In one aspect, an exemplary method includes mapping three dimensional data to a virtual space in augmented or virtual reality. The method also includes tracking a real position and orientation of a movable controller in a real space, based on data produced by sensors in the real space. The method also includes converting the real position and orientation of the movable controller into a virtual position and orientation of the movable controller relative to the three dimensional data in the virtual space. The method further includes identifying a selected region of the three dimensional data, which is tethered to the virtual position and orientation of the movable controller, and rendering the three dimensional data in the virtual space, with the selected region being rendered differently from the remainder of the three dimensional data.

According to another aspect, an exemplary apparatus for rendering internal structures of a three dimensional model in augmented reality or virtual reality includes: a memory that embodies program data, which includes three dimensional data and computer executable instructions; sensors that produce data related to a real position and orientation of a movable controller in a real space; and at least one processor, connected in communication with the memory and the sensors. The at least one processor is operative by the computer executable instructions to facilitate a method that includes several steps. The method includes mapping the three dimensional data to a virtual space in augmented or virtual reality; tracking the real position and orientation of the movable controller, based on data produced by the sensors in the real space; converting the real position and orientation of the movable controller into a virtual position and orientation of the movable controller relative to the three dimensional data in the virtual space; identifying a selected region of the three dimensional data, which is tethered to the virtual position and orientation of the movable controller; rendering the three dimensional data in the virtual space with the selected region being rendered differently from the remainder of the three dimensional data; and showing a user the rendering of the three dimensional data in the virtual space by activating a virtual or augmented reality display.

One or more embodiments of the invention or elements thereof can be implemented in the form of a computer program product including a computer readable storage medium with computer usable program code for facilitating the method steps indicated. Furthermore, one or more embodiments of the invention or elements thereof can be implemented in the form of a system (or apparatus) including a memory that embodies computer executable instructions, and at least one processor that is coupled to the memory and operative by the instructions to facilitate exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a tangible computer readable storage medium (or multiple such media) and implemented on a hardware processor, or (iii) a combination of (i) and (ii); any of (i)-(iii) implement the specific techniques set forth herein.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

In view of the foregoing, techniques of the present invention can provide substantial beneficial technical effects. For example, one or more embodiments provide one or more of:

Improved visualization of internal structures of 3-D models.

More efficient calculation of 3-D model representations.

Rendering of a 3-D model with reduced draw calls due to improved culling of non-visible structure.

More intuitive user interface, allowing natural interaction with both tactile and sensorimotor learning over data that is otherwise only visually inspected.

Rapid responsiveness to user movements, including rotation, penetration, and scaling, in a simulated 3-D environment.

Orientation can match that of a surgical approach, probe insertion, or injury angle.

These and other features and advantages of the present invention will become apparent from the following detailed description of illustrative embodiments thereof, which is to be read in connection with the accompanying drawings.

DETAILED DESCRIPTION

Figure 2:
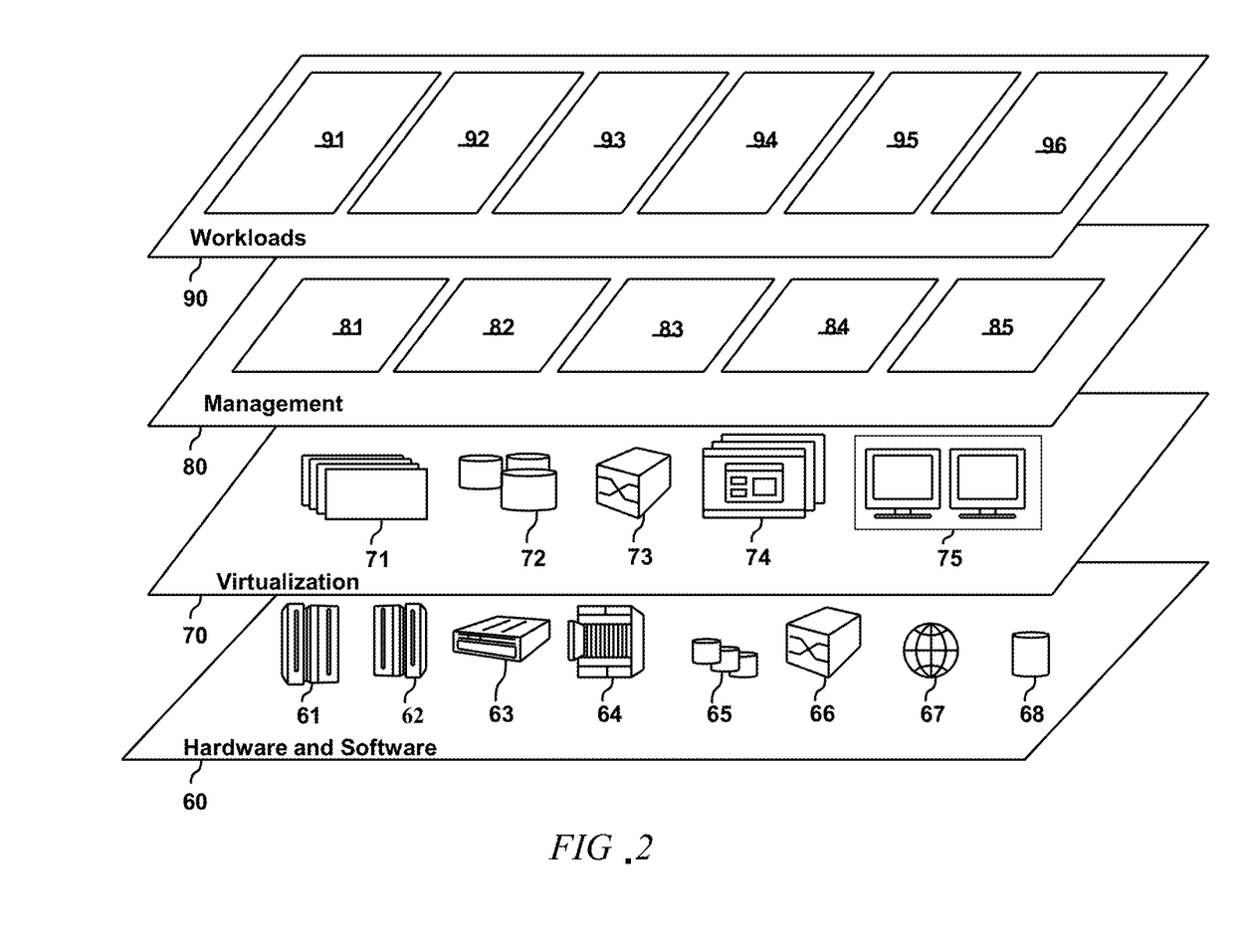
FIG. 2 depicts abstraction model layers according to an embodiment of the present invention.

As will be appreciated from the foregoing, it is desirable to improve the visualization of three dimensional data. For this purpose, the present invention provides a data visualization system 96, as depicted in FIG. 2.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
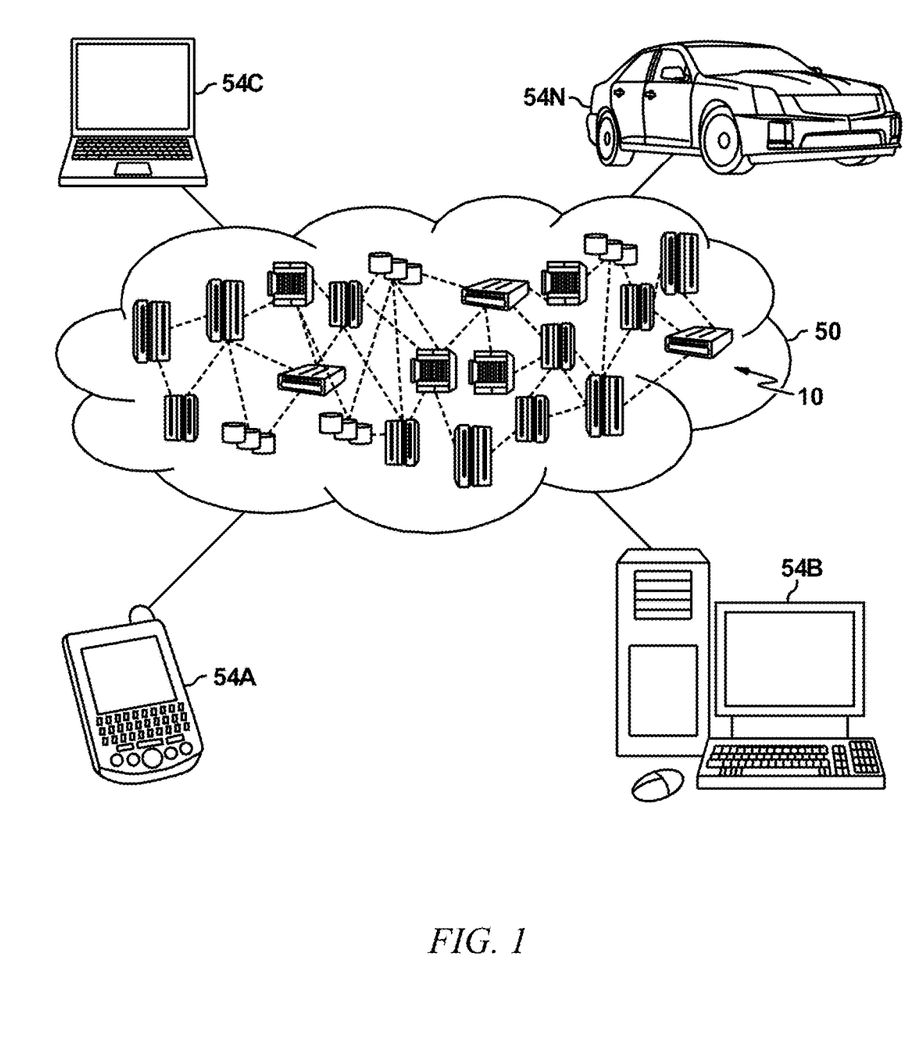
FIG. 1 depicts a cloud computing environment according to an embodiment of the present invention.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a data visualization system 96.

Figure 3:
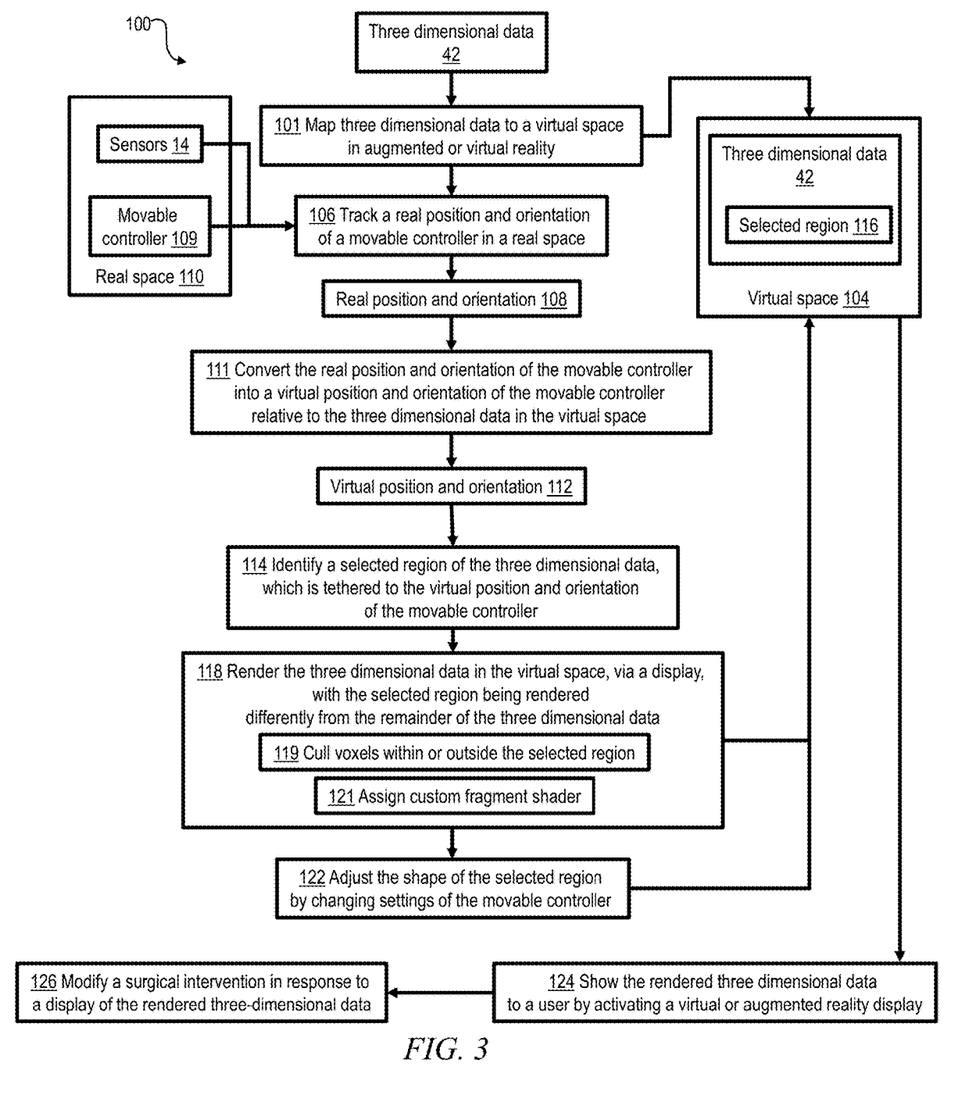
FIG. 3 depicts in a flowchart a method for visualizing internal structures of a 3-D model, according to an exemplary embodiment.

FIG. 3 depicts in a flowchart a method 100 that is implemented by the data visualization system 96, using one or more of the cloud computing node(s) or computing apparatus 10, for visualizing internal structures of a 3-D model. One advantage of the method 100 is the possibility of slicing a 3-D model (e.g., a brain volume) dynamically and in real-time through the use of augmented reality or virtual reality (AR/VR) hand controllers.

At 101, the method 100 includes mapping three dimensional data 42 (the 3-D model) to a virtual space 104 in augmented or virtual reality. That is, a file containing 3-D or 4-D data is parsed and converted into a floating value 3-D matrix. In case of 4-D input (e.g. RGBA data), the first three dimensions represent the position in the matrix and the fourth dimension represents the value ("color") of a cell ("voxel").

At 106, the method includes tracking a real position and orientation 108 of a movable controller 109 in a real space 110, using data from sensors 14. In one or more embodiments, the movable controller 109 houses one or more of the sensors 14. In one or more embodiments, at least one of the sensors 14 is external to the movable controller 109. At 111, convert the real position and orientation 108 of the movable controller into a virtual position and orientation 112 of the movable controller 109 relative to the three dimensional data 42 in the virtual space 104. At 114, identify a selected region 116 of the three dimensional data 42, which is tethered to the virtual position and orientation 112 of the movable controller 109. That is, either through outside-in or inside-out AR/VR tracking, the 3-D position and orientation of one or multiple controllers is computed. An "excluder" (or exclusion cube) that identifies the selected region 116 is positioned in correspondence with these controllers, and is moved accordingly.

At 118, render the three dimensional data 42 in the virtual space 104 with the selected region 116 being rendered differently from the remainder of the three dimensional data 42. In one or more embodiments, the three dimensional data 42 is converted into a 3-D texture and rendered as a voxel array or through a standard volume renderer. The rendered volume is inserted into a 3-D scene (the virtual space 104) at an arbitrary position, and oriented and scaled as required.

In one or more embodiments, the selected region 116 is an exclusion region and the three dimensional data 42 within the selected region 116 is marked not to be rendered while the three dimensional data 42 outside the selected region 116 is marked to be rendered. In such embodiments, during the rendering pipeline, primitives originating from the three dimensional data 42 (e.g., brain volume data) are discarded (culled) at 119 whenever they intersect an "excluder" object (i.e. the selected region 116), based on the concept of culling. This operation prevents these primitives from progressing in the rendering pipeline, reducing the number of draw calls and improving performance.

In one or more embodiments, the selected region 116 is an inclusion region and the three dimensional data 42 within the selected region 116 is marked to be rendered while the three dimensional data 42 outside the selected region 116 is marked not to be rendered. In such embodiments, during the rendering pipeline, primitives originating from the three dimensional data 42 are discarded (culled) at 119 unless they intersect an "includer" object, i.e. the selected region 116.

In one or more embodiments, the method 100 also includes, at 121, assigning to each excluder a material with a custom fragment shader, which prevents writing to the depth and color buffers and makes the excluder transparent (i.e. the inside of its volume appears as "empty").

In one or more embodiments, the method 100 also includes, at 122, adjusting the shape of the selected region 116 by changing settings of the movable controller 109.

Once the three dimensional data has been rendered in the virtual space, another step of the method 100 is, at 124, to show the rendered three dimensional data to a user by activating a virtual or augmented reality display. In one or more embodiments, at 126 the user modifies a surgical intervention in response to the display of the rendered data.

Figure 4:
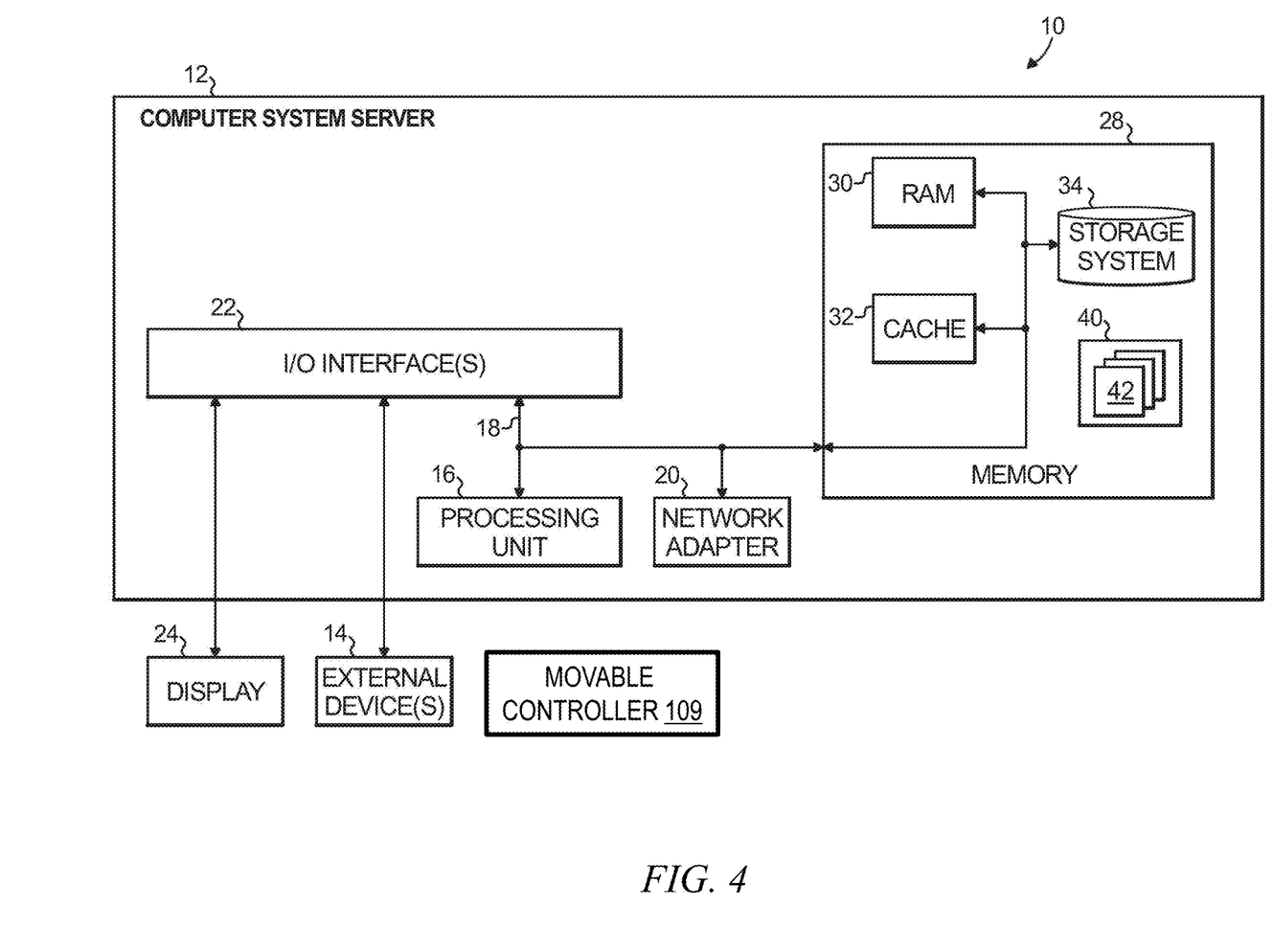
FIG. 4 depicts in a schematic an apparatus for implementing the method of FIG. 3, according to an exemplary embodiment.

Referring to FIG. 4, an apparatus 10 (further discussed below) for implementing the method 100 includes a computer processing unit 16 (e.g., a graphics processing unit), a virtual reality or augmented reality display 24 (e.g., smart goggles), and a database 40 that stores the three-dimensional data 42, in combination with a plurality of external devices (i.e. sensors) 14 that produce data about the real position and orientation of the movable controller 109. In one or more embodiments, the movable controller 109 is a wireless handheld controller that is operable by touch controls. Non-limiting exemplary embodiments of the movable controller 109, according to the apparatus 10, include a mobile phone, a game controller, a glove, or a wand. In one or more embodiments, multiple movable controllers may be employed simultaneously. In one or more embodiments, some or all of the sensors 14 may be internal to the movable controller 109.

Figure 6:
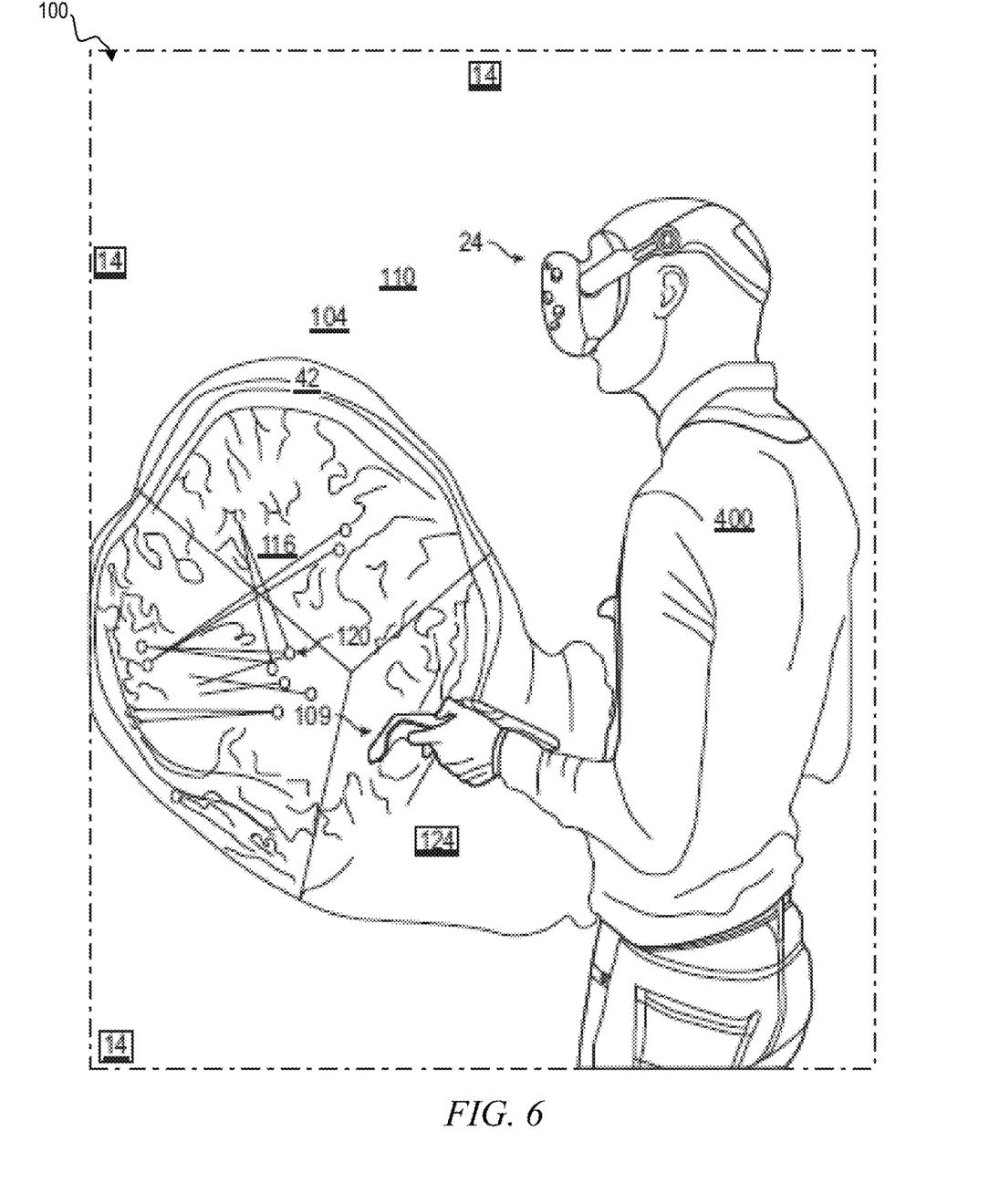
FIG. 6 depicts in a schematic an operational example of the method and apparatus of FIGS. 3 and 4, according to an exemplary embodiment

Referring also to FIGS. 3 and 6, the computer processing unit 16 tracks the real position and orientation 108 of the movable controller 109 by calculating the real position and orientation based on the data produced by the sensors 14. In one or more embodiments, the computer processing unit 16 converts the real position and orientation 108 into the virtual position and orientation 112 by comparison of the real position and orientation to a zero reference position and orientation 124 in the real space 110. The zero reference position and orientation 124 may be determined by an inertial tracker (e.g., accelerometer, gyro sensor), by a calibrated camera system, by a plurality of antennas or microphones receiving wireless signals from the movable controller 109, etc. and each of these modes for determining the zero reference position and orientation may serve as one or more of the sensors 14. In one or more embodiments, scaling factors are applied during the comparison so that movement of the movable controller 109 to change the real position and/or orientation 108 by a first amount will change the virtual position and/or orientation 112 by a second, different amount. In one or more embodiments, the real position and/or orientation 108 is changed by a first amount that changes the virtual position and/or orientation 112 by a second amount, the second amount determined by a precalculated feature of interest in the 3D image and by a simulated detent in the movable controller oriented relative to that feature. In this way, the user experiences resistance to moving away from a position where a precalculated feature is oriented optimally and revealed by use of an excluder. In this context, a "simulated detent" is a programming feature that causes the movable controller 109 to vibrate or otherwise present real or simulated resistance to motion when the user tries to remove the movable controller from a real position and/or orientation that corresponds to a virtual position and/or orientation that is identified by the detent. Simulated resistance in this case is represented by a resistance in the transformation of the virtual position and/or orientation based on the movable controller's movement through a real position and/or orientation A simulated detent may be set up by the user selecting a feature of interest; the virtual position and/or orientation of the feature of interest then can be identified by a neural network that pattern-matches a template anatomy of the feature to a feature of the three-dimensional data 42. A simulated detent may also be set up in a completely unsupervised manner. For example, certain segmentation data may be collected based on the boundaries of certain changes in voxel values in a data set, representing the boundary of a putative object in the rendered data space. These boundaries may then be used to extract a set of boundary points within the 3-dimensional hull of the data 42. By performing Principal Component Analysis on these points, the longest and second longest orthogonal axes in 3-dimensions can be determined, defining a plane and orientation for the creation of a simulated detent. In one or more embodiments, the term "anatomy" refers not only to human or animal physiology but also to mechanical structure such as, by way of non-limiting examples, the components of an airframe or a hydraulic system or the layers and gates of a semiconductor wafer.

Figure 5:
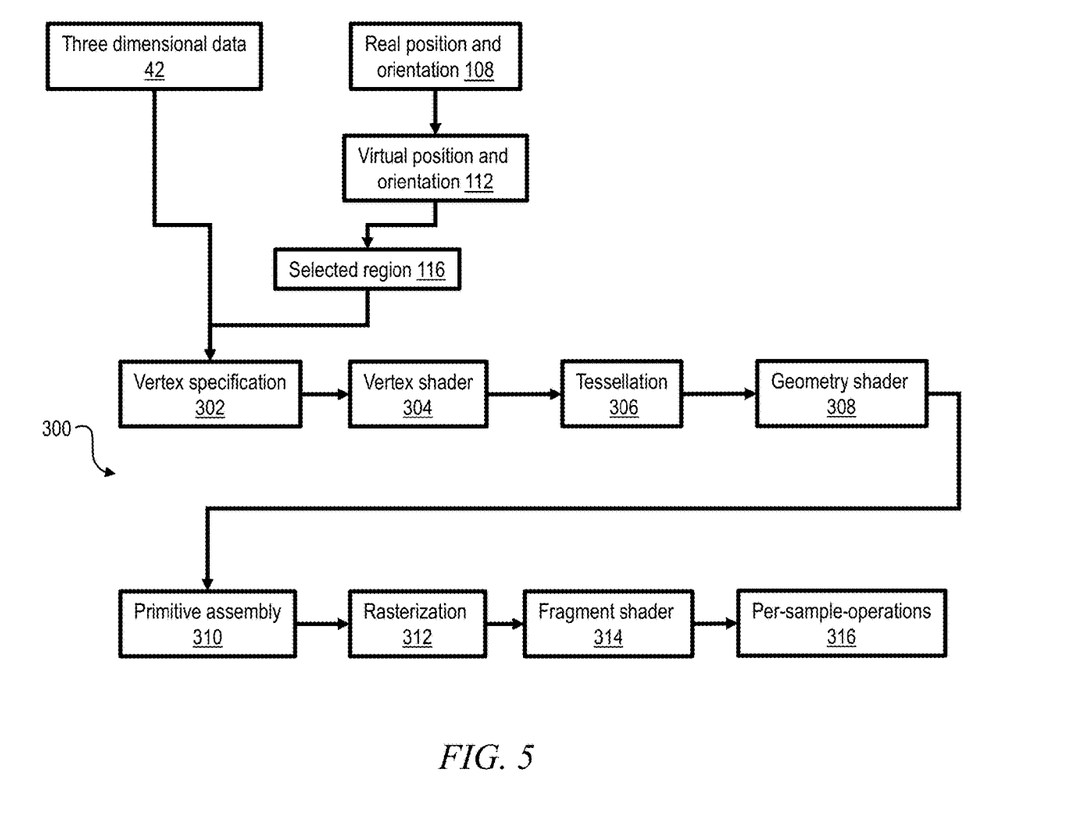
FIG. 5 depicts in a flowchart a rendering pipeline for implementing the method of FIG. 3, according to an exemplary embodiment.

FIG. 5 depicts in a flowchart a method (rendering pipeline) 300 for rendering the three-dimensional data 42 in the virtual space 104, taking into account the selected region 116. In one or more embodiments, the rendering pipeline 300 is based on a standard OpenGL pipeline. Thus, it receives as its inputs the three dimensional (or four dimensional) data 42 as well as the real position and orientation 108 of the movable controller 109. In a pre-processing stage the real position and orientation 108 are converted to the virtual position and orientation 112, based on which the selected region 116 is identified. Then the three dimensional data 42 and the selected region 116 feed into a vertex specification module 302. The workflow proceeds to a vertex shader 304, tessellation 306, and a geometry shader 308. However, unlike the standard OpenGL pipeline, in one or more embodiments the rendering pipeline 300 cuts or "culls" primitive shapes (i.e. the selected region(s) 116) out of the volume of three-dimensional data 42 by discarding voxels that intersect with any excluder object. This procedure, shown at 119 in FIG. 3, advantageously reduces the number of draw calls, increasing the overall performance. The procedure can be performed in various ways, including the use of z-buffers and other hidden-surface determination algorithms. However, instead of or in addition to discarding elements with z-value greater than a certain amount (occlusion), embodiments of the invention discard elements with a z-value in between the two values associated to the boundaries of the excluder cube (selected region 116).

The culling procedure can be performed either during primitive assembly 310, during rasterization 312, or during per-sample-operations stages 316, and may be accelerated on the GPU (computer processing unit), depending on the specific culling algorithm implemented. In one or more embodiments, the culling procedure is implemented only in one of the rendering stages, not redundantly at all three rendering stages.

In the fragment shader 314, the volume occupied by each excluder (selected region 116) is completely transparent, allowing rendering of internal regions of the 3-D model (e.g., a brain model). That is, referring briefly back to FIG. 3, each excluder (selected region 116) is assigned at 121 a material with a custom fragment shader, which prevents writing to the depth and color buffers and makes the excluder transparent (i.e. the inside of its volume appears as "empty"). Sample shader parameters for the selected region 116 include:

ZWRITE=OFF->Disables writing pixels to the depth buffer.

ColorMask=0->Turns off rendering to all color channels.

In other embodiments, elements not within the selected region 116 are discarded and only those elements within boundaries of the selected region 116 are rendered.

With attention now to FIG. 6, which depicts in a schematic an operational example of the method 100 being implemented with the virtual space 104 overlaid in the real space 110, the three dimensional data 42 is rendered in the virtual space 104 with the selected region(s) 116 culled, and is displayed to the user 400 via the display 24. The user 400 wields the movable controller(s) 109 to adjust the position and orientation of the selected region(s) 116.

In one or more embodiments, the computer processing unit 16 identifies the selected region 116 in response to settings of the movable controller 109, e.g., in response to button presses or to touch screen gestures. For example, in one or more embodiments, the selected region 116 is centered on the movable controller 109. In one or more embodiments, a vertex 120 (e.g., a corner or center) of the selected region 116 is tethered to the movable controller 109.

In another embodiment, a user's appendage (e.g., a hand) is utilized as the movable controller 109. In such an embodiment, the sensors 14 are external to the appendage. Non-limiting examples of data received from the sensors 14 include visible light camera images, radar returns, infrared beam reflections, etc.

Given the discussion thus far, it will be appreciated that, in general terms, an exemplary method 100, according to an aspect of the invention, includes, as at 101, mapping three dimensional data 42 to a virtual space 104 in augmented or virtual reality. Also included is step 106, tracking a real position and orientation 108 of a movable controller 109 in a real space 110, based on data produced by sensors 14 in the real space. In step 111, convert the real position and orientation of the movable controller into a virtual position and orientation of the movable controller relative to the three dimensional data in the virtual space. At 114, identify a selected region 116 of the three dimensional data, which is tethered to the virtual position and orientation of the movable controller. At 118, render the three dimensional data in the virtual space, with the selected region being rendered differently from the remainder of the three dimensional data.

In one or more embodiments, the selected region 116 is an exclusion region and the three dimensional data 42 within the selected region is marked not to be rendered while the three dimensional data outside the selected region is marked to be rendered. For example, the method 100 may include, at 119, culling voxels from the three dimensional data within the selected region.

In one or more embodiments, the selected region is an inclusion region and the three dimensional data within the selected region is marked to be rendered while the three dimensional data outside the selected region is marked not to be rendered. For example, the method 100 may include, at 119, culling voxels from the three dimensional data outside the selected region.

In one or more embodiments, the method 100 also includes, at 121, assigning to voxels of the three dimensional data within the selected region a material with a custom fragment shader that is set to be transparent.

One or more embodiments also include, at 122, adjusting the shape of the selected region by changing settings of the movable controller.

In one or more embodiments, the method 100 also includes, at 114, tethering the selected region to the virtual position and orientation by a simulated detent.

In one or more embodiments, at 126, show the rendered three dimensional data to a user by activating a virtual or augmented reality display.

In at least one embodiment, the method 100 also includes, at 128, modifying a surgical intervention in response to a display of the rendered three-dimensional data.

According to another aspect of the invention, an exemplary apparatus for rendering internal structures of a three dimensional model in augmented reality or virtual reality includes: a memory 28 embodying program data, which includes three-dimensional data 42 as well as computer executable instructions; sensors 14 that produce data related to the position and orientation 108 of a movable controller 109 in a real space 110; at least one processor 16, coupled to the memory 28 and to the sensors 14, and operative by the computer executable instructions to carry out or otherwise facilitate one or more embodiments of the method 100 and to show a user the rendering of the three dimensional data in the virtual space by activating a virtual or augmented reality display 24.

In one or more embodiments, the movable controller 109 is a wireless handheld controller that houses at least one of the sensors 14 and is operable by touch controls (by way of non-limiting examples, a button, a joystick, a touchpad, a rocker switch).

According to another aspect of the invention, a non-transitory computer readable medium embodies computer executable instructions, which when executed by a computer cause the computer to carry out or otherwise facilitate any one, some, or all of the method steps disclosed herein.

One or more embodiments of the invention, or elements thereof, can be implemented in the form of an apparatus including a memory and at least one processor that is coupled to the memory and operative to perform exemplary method steps, or in the form of a non-transitory computer readable medium embodying computer executable instructions which when executed by a computer cause the computer to perform exemplary method steps. Referring again to FIG. 4, in the apparatus 10 (which may be in one or more embodiments a cloud computing node, or in one or more other embodiments a standalone computing apparatus) there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in apparatus 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

A database 40, containing the three dimensional data 42 as well as other program data, may be stored in one or more components of the system memory 28. Program data may include an operating system, one or more application programs, other program modules, and computer executable instructions for manipulating, mapping, and rendering the three dimensional data. Each of the operating system, one or more application programs, other program modules, and computer executable instructions, or some combination thereof, may include an implementation of a networking environment. Program modules generally carry out the functions and/or methodologies of embodiments of the invention as described herein.

Computer system/server 12 may also communicate with one or more external devices such as a keyboard, a pointing device, the sensors 14, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 4, such an implementation might employ, for example, the processor 16, the system memory 28, and an input/output interface 22 to the display 24 and to external device(s) such as a keyboard, a pointing device, the sensors 14, or the like. The term "processor" as used herein is intended to include any processing device, such as, for example, one that includes a CPU (central processing unit), a GPU (graphics processing unit), and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 4) running a server program. It will be understood that such a physical server may or may not include a display and keyboard.

One or more embodiments can be at least partially implemented in the context of a cloud or virtual machine environment, although this is exemplary and non-limiting.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   mapping three dimensional data to a virtual space in augmented or virtual reality;
   tracking a real position and orientation of a movable controller in a real space, based on data produced by sensors in the real space;
   converting the real position and orientation of the movable controller into a virtual position and orientation of the movable controller relative to the three dimensional data in the virtual space;
   identifying a selected region of the three dimensional data, which is tethered to the virtual position and orientation of the movable controller;
   setting up a simulated detent by:
   collecting segmentation data based changes in voxel values in the three dimensional data;
   extracting a set of boundary points from a 3-dimensional hull of the segmentation data;
   determining longest and second longest orthogonal axes in 3-dimensions of the segmentation data by performing Principal Component Analysis on the boundary points; and
   defining a plane and orientation for creation of the simulated detent based on the longest and second longest orthogonal axes;
   rendering the three dimensional data in the virtual space, with the selected region being rendered differently from the remainder of the three dimensional data;
   showing a user the rendering of the three dimensional data in the virtual space by activating a virtual or augmented reality display; and
   activating a haptic feedback of the movable controller in response to the virtual position and orientation matching the simulated detent.

2. The method of claim 1 wherein the selected region is an exclusion region and the three dimensional data within the selected region is marked not to be rendered while the three dimensional data outside the selected region is marked to be rendered.

3. The method of claim 2 further comprising culling voxels from the three dimensional data within the selected region during primitive assembly.

4. The method of claim 1 wherein the selected region is an inclusion region and the three dimensional data within the selected region is marked to be rendered while the three dimensional data outside the selected region is marked not to be rendered.

5. The method of claim 4 further comprising culling voxels from the three dimensional data outside the selected region.

6. The method of claim 1 further comprising assigning to voxels of the three dimensional data within the selected region a material with a custom fragment shader that is set to be transparent.

7. The method of claim 1 further comprising adjusting the shape of the selected region by changing settings of the movable controller.

8. The method of claim 1 further comprising modifying a surgical intervention in response to a display of the rendered three-dimensional data.

9. An apparatus for rendering internal structures of a three dimensional model in augmented reality or virtual reality, the apparatus comprising:
   a memory that embodies program data, which includes three dimensional data and computer executable instructions;
   sensors that produce data related to a real position and orientation of a movable controller in a real space;
   at least one processor, connected in communication with the memory and the sensors, and operative by the computer executable instructions to facilitate a method of:
   mapping the three dimensional data to a virtual space in augmented or virtual reality;
   tracking the real position and orientation of the movable controller, based on data produced by the sensors in the real space;
   converting the real position and orientation of the movable controller into a virtual position and orientation of the movable controller relative to the three dimensional data in the virtual space;
   identifying a selected region of the three dimensional data, which is tethered to the virtual position and orientation of the movable controller;
   setting up a simulated detent by:
   collecting segmentation data based changes in voxel values in the three dimensional data;
   extracting a set of boundary points from a 3-dimensional hull of the segmentation data;
   determining longest and second longest orthogonal axes in 3-dimensions of the segmentation data by performing Principal Component Analysis on the boundary points; and
   defining a plane and orientation for creation of the simulated detent based on the longest and second longest orthogonal axes;

rendering the three dimensional data in the virtual space with the selected region being rendered differently from the remainder of the three dimensional data;

showing a user the rendering of the three dimensional data in the virtual space by activating a virtual or augmented reality display; and activating a haptic feedback of the movable controller in response to the virtual position and orientation matching the simulated detent.

10. The apparatus of claim 9 wherein the movable controller is a wireless handheld controller that houses at least one of the sensors and is operable by touch controls.

11. The apparatus of claim 9 wherein the selected region is an exclusion region and the three dimensional data within the selected region is marked not to be rendered while the three dimensional data outside the selected region is marked to be rendered.

12. The apparatus of claim 11 wherein the method further comprises culling voxels from the three dimensional data within the selected region during primitive assembly.

13. The apparatus of claim 9 wherein the selected region is an inclusion region and the three dimensional data within the selected region is marked to be rendered while the three dimensional data outside the selected region is marked not to be rendered.

14. The apparatus of claim 13 wherein the method further comprises culling voxels from the three dimensional data outside the selected region.

15. The apparatus of claim 9 wherein the method further comprises assigning to voxels of the three dimensional data within the selected region a material with a custom fragment shader that is set to be transparent.

16. The apparatus of claim 9 wherein the method further comprises adjusting the shape of the selected region by changing settings of the movable controller.

17. A non-transitory computer readable medium embodying computer executable instructions which when executed by a computer cause the computer to facilitate a method of:

mapping three dimensional data to a virtual space in augmented or virtual reality;

tracking a real position and orientation of a movable controller in a real space, based on data produced by sensors in the real space;

converting the real position and orientation of the movable controller into a virtual position and orientation of the movable controller relative to the three dimensional data in the virtual space;

identifying a selected region of the three dimensional data, which is tethered to the virtual position and orientation of the movable controller;

setting up a simulated detent by:
    collecting segmentation data based changes in voxel values in the three dimensional data;
    extracting a set of boundary points from a 3-dimensional hull of the segmentation data;
    determining longest and second longest orthogonal axes in 3-dimensions of the segmentation data by performing Principal Component Analysis on the boundary points; and
    defining a plane and orientation for creation of the simulated detent based on the longest and second longest orthogonal axes;

rendering the three dimensional data in the virtual space with the selected region being rendered differently from the remainder of the three dimensional data;

showing a user the rendering of the three dimensional data in the virtual space by activating a virtual or augmented reality display; and activating a haptic feedback of the movable controller in response to the virtual position and orientation matching the simulated detent.

\* \* \* \* \*